Dec. 18, 1951 P. SHAMBURGER Plant Pat. 1,054
ROSE PLANT
Filed Sept. 18, 1950
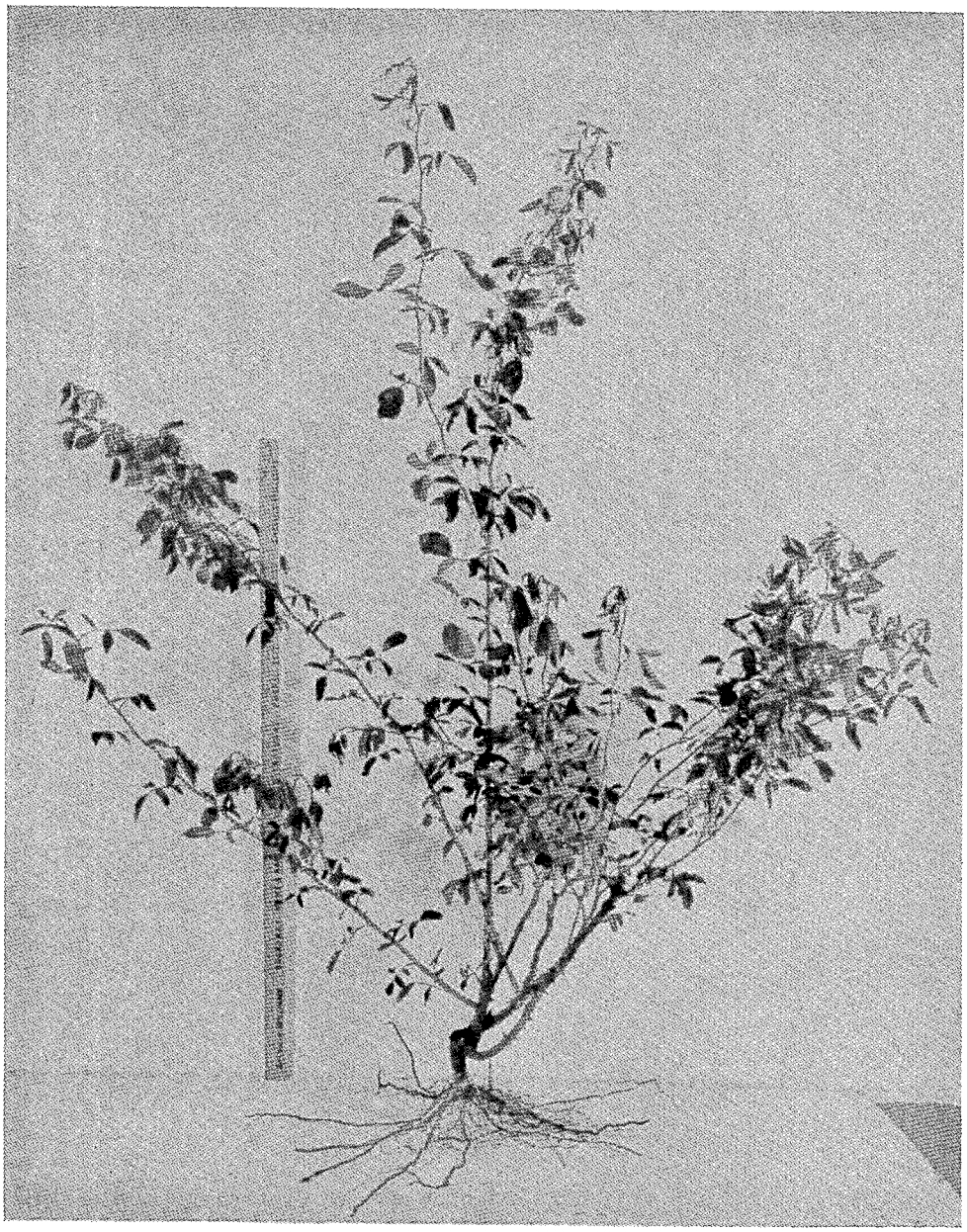
Inventor.
Paul Shamburger
By Robb & Robb
Attorneys.

Patented Dec. 18, 1951 Plant Pat. 1,054

UNITED STATES PATENT OFFICE 1,054

ROSE PLANT

Paul Shamburger, Tyler, Tex.

Application September 18, 1950, Serial No. 185,421

1 Claim. (Cl. 47—61)

The present invention relates to a new and distinct variety of rose plant, originated as a cultivated sport of the variety "Floradora" (unpatented), and distinguished therefrom by its climbing habit of growth, said sport having been discovered by me amongst cultivated plants in my nursery plantings on my property.

The parent variety is a bush rose of the polyantha class, and is notable for the imbricated arrangement of the petals of its flowers, by the long-lasting habit of the flowers both on the bush and as cut-flowers, and by their unique color effect which is maintained to an extraordinary degree throughout the blooming season.

Of primary importance here, however, is the fact that this parent variety has never, so far as I am aware, exhibited a climbing habit, and its growth has been that of the average strong bush rose.

Aside from the climbing habit of this new variety, it is generally similar to its parent "Floradora," and attains its desirable and superior qualities which are unique in a climbing rose.

Asexual reproduction of the new variety by budding at Tyler, Texas, shows that the foregoing characteristics come true and are established and transmitted through succeeding propagations.

The accompanying drawing shows a specimen plant of the new variety in comparison with a measuring scale (yardstick) to illustrate its dominant climbing habit of growth.

The following is a detailed description of the new variety, with color terminology in accordance with Ridgway's Color Standards and Nomenclature, except where color terms of ordinary dictionary significance are obvious:

Type: Hardy; climbing; sport; for cut flowers and garden decoration.
Class: Hybrid polyantha.
Parentage: Sport of "Floradora."
Propagation: Holds its distinguishing characteristics through succeeding propagations by budding, which is the only method tried up to the present time.

*Flower*

Locality where grown: Tyler, Texas.
Flowers borne: Singly; irregular; on strong, short stems.
Quantity of bloom: Moderate, outdoors.
Continuity: Continuous.
Fragrance: Slight, spicy.
Bud:
*Peduncle.*—Medium length; medium heavy; erect; medium Reddish-Green color; almost smooth; few brown hairs.

*Before calyx breaks.*—Size—medium.—Form—pointed; with foliaceous appendages (sepals) on the surface of the bud; with slender, much cut, foliaceous parts extending beyond the top of the bud equal to ¾ or more of its length.
*As calyx breaks.*—Color—Carmine, Plate I.
*As first petal opens.*—Size—small.—Form—short, globular. Color—outside: Nopal-Red, Plate I; inside: Scarlet-Red, Plate I.
*Opening.*—Opens up well.
Bloom:
*Size.*—Medium; 2½ to 2¾ inches.
*Petalage.*—Very double, with no stamens showing; from fifty to fifty-five petals arranged irregularly.
*Form.*—Cupped, full at first; becoming open, cupped; petals being at first tightly cupped, rolled inward; becoming later, at maturity, tightly flat, rolled outward.
Petals: Soft, with inside satiny and outside shiny.
*Shape.*—Outside—obovate, scalloped with apex flat, with 1 notch. Intermediate—obovate, scalloped with apex flat, with 1 notch. Inside—ovate, with apex flat.
*General color effect.*—Newly opened flower—Scarlet, Plate I. Three days open—Peach-Red, Plate I.
*Behavior.*—Drop off cleanly; fading brown; withstands hot, dry weather.
*Flower longevity.*—On bush in garden, five days in July; cut roses grown outdoors, kept at living-room temperatures five days in July.

*Reproductive organs*

Stamens: Few; arranged irregularly about pistils, mixed with petaloids.
Filaments: Short; Pale Ochraceous-Buff, Plate XV; few with anthers.
Anthers: Very small; Ochraceous-Buff Plate XV; open at various times.
Pollen: Very sparse; Mars-Yellow, Plate III.
Pistils: Few
Styles: Uneven; medium length; thin; columnar.
Stigma: White.
Ovaries: All enclosed in calyx.
Hips: None as yet have appeared.
Sepals: Permanent; moderately long; spear-shaped; recurved.

*Plant*

Foliage:
*Leaves.*—Compound of 3, 5 leaflets; abundant; moderately large; leathery; glossy.

*Leaflets.*—With apex obtuse; base round; margin simply serrate.

*Color.*—Mature—upper surface: Varley's Green, Plate XVIII; under surface: Light Elm-Green, Plate XVII. Young—upper surface: Argus Brown, Plate III, on Olive-green, Plate IV; under surface: Raw Umber, Plate III, with Argus Brown ribs, Plate III.

*Rachis.*—(The supporting stem of the compound leaf)—medium heavy. Upper side—smooth; grooved. Under side—moderately thorny.

*Stipules.*—Moderately short; medium width; with medium long points, turning out at an angle of more than 45°, recurved toward the stem.

*Disease.*—Resistant to mildew and black-spot.

Growth:

*Habit.*—Upright; climbing; much branched.

*Growth.*—Vigorous.

*Canes.*—Medium heavy.

*Main stems.*—Bright green. Thorns—several; medium length; hooked downward; with short narrow base. Prickles—none. Hairs—none.

*Branches.*—Dull green. Thorns—several; hooked downward; with narrow base. Prickles—none. Hairs—none.

*New shoots.*—Bright green. Thorns—several; medium length; hooked downward; with short, narrow base. Prickles—none. Hairs—none.

I claim:

A new and distinct variety of rose plant of the hybrid polyantha class, characterized as to novelty by its general similarity to its parent "Floradora" (unpatented), but distinguished therefrom by its strong and vigorous climbing habit of growth, substantially as shown and described.

PAUL SHAMBURGER.

No references cited.